(12) United States Patent
Scheeline

(10) Patent No.: US 10,324,023 B1
(45) Date of Patent: Jun. 18, 2019

(54) ENERGY DISPERSION CUVETTE

(71) Applicant: SpectroClick, Inc., Campaign, IL (US)

(72) Inventor: Alexander Scheeline, Champaign, IL (US)

(*) Notice: Subject to any disclaimer, the term of this patent is extended or adjusted under 35 U.S.C. 154(b) by 14 days.

(21) Appl. No.: 15/379,462

(22) Filed: Dec. 14, 2016

Related U.S. Application Data

(60) Provisional application No. 62/267,163, filed on Dec. 14, 2015.

(51) Int. Cl.
  *G01N 21/03* (2006.01)
  *G01J 3/18* (2006.01)

(52) U.S. Cl.
  CPC ............ *G01N 21/0303* (2013.01); *G01J 3/18* (2013.01); *G01J 2003/1861* (2013.01); *G01N 2021/036* (2013.01); *G01N 2021/0378* (2013.01)

(58) Field of Classification Search
  CPC ............ G01N 2021/0385; G01N 21/03–21/09
  USPC ................................................ 356/244–246
  See application file for complete search history.

(56) References Cited

U.S. PATENT DOCUMENTS

| | | | | |
|---|---|---|---|---|
| 3,612,697 A * | 10/1971 | Nebe | ............... | G01N 21/4133 250/576 |
| 5,100,238 A * | 3/1992 | Nailor | ............... | G01N 21/51 356/246 |
| 5,121,988 A * | 6/1992 | Blesener | ............... | G01N 15/1434 250/574 |
| 5,347,358 A * | 9/1994 | Nebe | ............... | G01N 21/0303 356/128 |
| 5,854,685 A * | 12/1998 | Levine | ............... | G01J 3/1838 356/440 |
| 6,565,815 B1 * | 5/2003 | Chang | ............... | B01L 3/505 250/238 |
| 8,885,161 B2 | 11/2014 | Scheeline et al. | | |
| 2003/0049693 A1 * | 3/2003 | Goh | ............... | G01N 33/54373 435/7.9 |
| 2013/0093936 A1 * | 4/2013 | Scheeline | ............... | G01J 3/42 348/345 |
| 2014/0192350 A1 * | 7/2014 | Jeannotte | ............... | G01N 21/05 356/130 |
| 2015/0253244 A1 * | 9/2015 | Mander | ............... | G01N 21/01 356/51 |

OTHER PUBLICATIONS

Scheeline, Alexander, BUI, Thu Anh, Stacked, Mutually Rotated Diffraction Gratings as Enablers of Portable Visible Spectrometry, Applied Spectroscopy, 2016, 766-777, vol. 70(5), Society for Applied Spectroscopy.

* cited by examiner

*Primary Examiner* — Michael P LaPage
(74) *Attorney, Agent, or Firm* — Singleton Law Firm, P.C.

(57) ABSTRACT

The invention provides a combination of a sample container and energy dispersion device. Among possible applications is construction of compact spectrometers optimized for single use. The sample container includes diffraction gratings such that, when the container is illuminated with collimated light and observed with optics focused at infinity, one obtains an optical spectrum useful for identifying and measuring the concentration of specimens placed in the container, applicable for chemical analysis and for screening fluids for chemical or biological analysis. The invention further provides methods to fabricate a combination of a sample container and energy dispersion device, wherein one such method utilizes temperature controlled templates to emboss gratings on outside and inside faces of a cuvette.

9 Claims, 9 Drawing Sheets

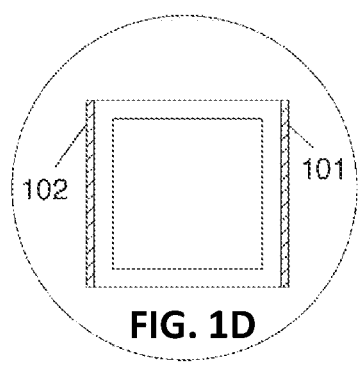
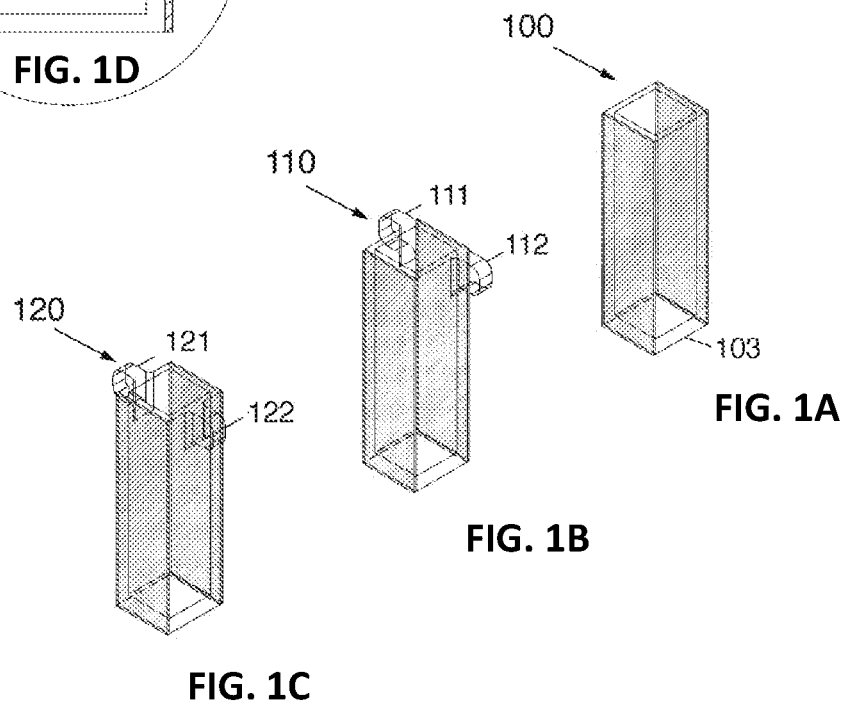
FIG. 1D
FIG. 1A
FIG. 1B
FIG. 1C

FIG. 4 EXPANDED

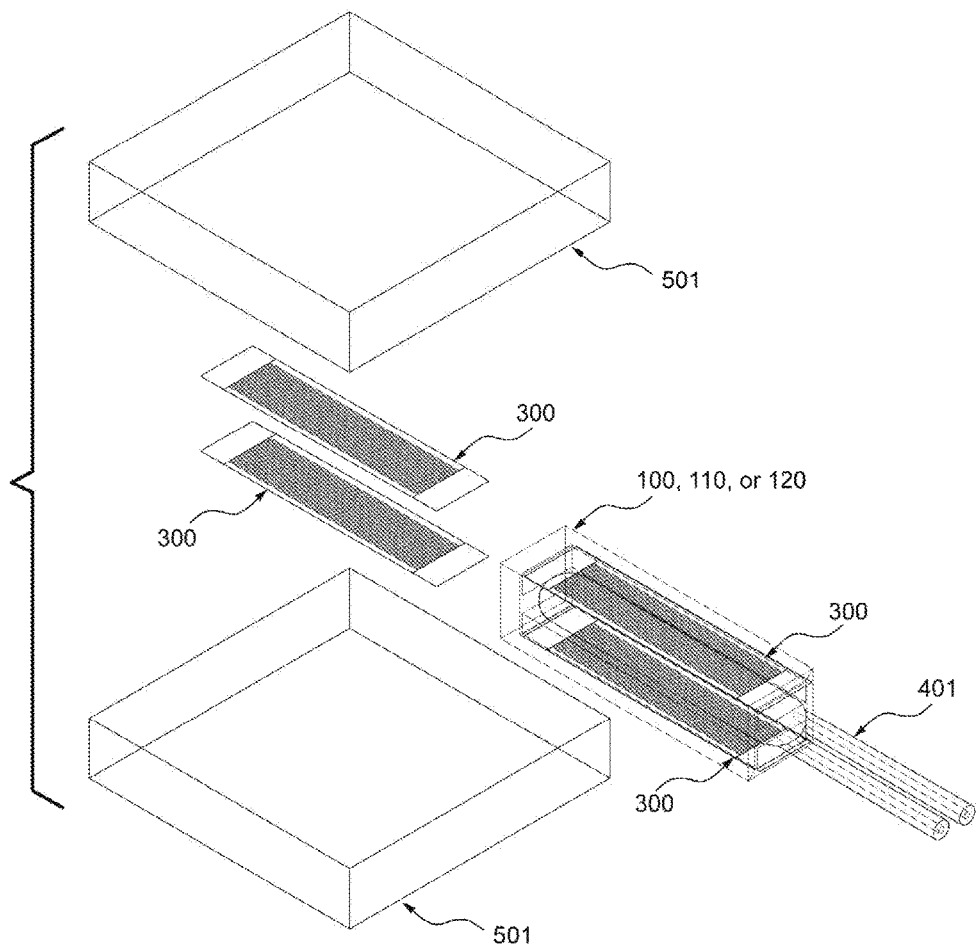
FIG. 6 EXPANDED

ENERGY DISPERSION CUVETTE

CROSS-REFERENCE TO RELATED APPLICATIONS

None.

BACKGROUND OF THE INVENTION

A cuvette is a container, transparent in at least one direction at wavelengths of interest for a particular spectrometric measurement. Such containers are routinely employed in optical spectrometry, such as in the application of absorption spectrometry.

One common design for a cuvette is a square prism, open at one end to allow admission and removal of liquid specimens. At least two opposite sides of the prism are transparent, optically flat, and slightly wedged so that the device does not act as a Fabry Perot interferometer. All four rectangular walls may optionally be transparent. Commonly, the non-transparent walls are translucent rather than opaque. While a geometry in which the cuvette is 4.5 cm tall with inside cross section a 1.0 cm square, cross sections from 1 mm (parallel to the light path) by 1 cm to 10 cm (parallel to the light path) by 1 cm are common. Another common design is a cylinder with a side port allowing admission and removal of liquid specimens. In this case, the end caps of the cylinder are transparent and optically flat.

Many materials have been used for such cuvettes, with glass, quartz, polystyrene, polycarbonate, and polymethylmethacrylate widely available. Among other uses, such cuvettes are placed in the light beam of a spectrometer, photometer, colorimeter, or spectrophotometer so that liquids inside the cuvette may be assayed for light transmission or absorption, which are indirect measures of chemical concentration.

If not observed without modification, the light passed through such a cuvette is typically dispersed by a grating or prism, observed with an interferometer, or attenuated with a filter prior to detection. Such modification of the light beam allows selection of those wavelengths or frequencies of light most useful to a particular measurement purpose. A key point is that separation of light into its component colors, wavelengths, or frequencies is carried out separately from the cuvette or container. An exception to this separation of containing sample and separating wavelengths was disclosed in U.S. Pat. No. 8,885,161. Among the embodiments of that patent was the use of a disposable/single use cuvette onto one face of which two or more mutually-rotated diffraction gratings were attached. Importantly, the gratings were in close proximity to each other, effectively adjacent and in or about in contact with each other. This configuration generates a number of cylindrically-arranged multiple diffraction orders, such that dispersion is cylindrically-symmetrical.

BRIEF SUMMARY OF THE INVENTION

Embodiments of the present invention provide a cuvette having two or more gratings. At least one grating is on, in, or a part of one face of a cuvette and at least one grating is on, in, or a part of the opposite face or opposite side of the same face of the cuvette, oriented such that light passes through both gratings, the cuvette, and any matter contained in the cuvette (if both gratings are transmission gratings). If one of the gratings is a reflection grating, then light passes through the transmission grating both incident on and exiting the cuvette (either before or after traversing the sample in each direction), traversing the contents of the cuvette twice, but reflecting off of the reflection grating. Embodiments of the present invention further disclose a method by which said gratings may be embossed or pressed into cuvette surfaces.

It is commonly necessary when molding cuvettes that the faces be imperfectly parallel. The gratings on the cuvette faces are tilted at whatever angle or "draft" is necessary for release from the fabrication mold, a geometry that also avoids having the faces of the cuvette act as an unintended Fabry Perot interferometer. Typically, the gratings as practiced here are on the outside faces of the cuvette, but the disclosure applies equally to having gratings on the outside or inside faces, in any combination of two, three, or four of the cuvette/other material interfaces and with one, two, or more gratings on or integral to one, two, or more of the interfaces.

According to the present invention, while gratings may be in contact with each other and mutually rotated, they may also be separated by the wall of the cuvette, by the analyte solution, or both, and at least one grating is not in contact with the other or others. While the first embodiment in the present disclosure has the gratings on the outside walls of the cuvette, the disclosure applies equally if both are on the inside walls, or one is on an inside wall and one is on an outside wall, whether or not the two or more gratings share a common wall of the cuvette.

In one embodiment of the invention, a plastic cuvette with 1 cm pathlength as is commonly used by those skilled in the art of visible absorption spectrometry is modified by having double-dispersion gratings applied to the outside faces through which light travels as it traverses the cuvette, including the sample liquid contained in the cuvette. On one face, the grating is rotated so that one of its principal axes makes an angle of about 30 degrees with the vertical edge of the cuvette. On the opposite face, the grating is aligned so that the principal axis makes on angle of approximately 0 degrees with the vertical edge of the cuvette.

In another embodiment of the invention, a glass cuvette with 1 cm pathlength as is commonly used by those skilled in the art of visible absorption spectrometry is modified by having double-dispersion gratings applied to the outside faces through which light travels as it traverses the cuvette, including the sample liquid contained in the cuvette. On one face, the grating is rotated so that one of its principal axes makes an angle of about 30 degrees with the vertical edge of the cuvette. On the opposite face, the grating is aligned so that the principal axis makes on angle of approximately 0 degrees with the vertical edge of the cuvette.

In another embodiment of the invention, a quartz cuvette with 1 cm pathlength as is commonly used by those skilled in the art of visible absorption spectrometry is modified by having double-dispersion gratings applied to the outside faces through which light travels as it traverses the cuvette, including the sample liquid contained in the cuvette. On one face, the grating is rotated so that one of its principal axes makes an angle of 30 degrees with the vertical edge of the cuvette. On the opposite face, the grating is aligned so that the principal axis makes on angle of approximately 0 degrees with the vertical edge of the cuvette.

In other embodiments of the invention, instead of using a double dispersion grating, one, the other, or both gratings are replaced with single dispersion gratings, using glass, plastic, or quartz cuvettes.

In another embodiment of the invention, a plastic cuvette is fabricated with a periodic structure molded into each outside face of the cuvette through which light is transmitted. On one of these faces, the periodic structure is either a single or double-dispersion grating. On the other face, the periodic structure is either a single or double-dispersion grating, but the orientation of the periodic structure is rotated at a non-zero angle with respect to the grating on the opposite face. The spacing of the second grating is typically similar to that of the first, but need not be the same.

In another embodiment of the invention, a plastic cuvette of conventional design is imprinted with a periodic structure using microcontact printing. Commonly, the ink used in microcontact printing is polydimethylsiloxane, but other inks may be employed. The printed grating has a periodic structure in one or two dimensions and a thickness no less than 1 nm and no thicker than 1 mm. The structure printed on one transmissive face of the cuvette is typically aligned parallel to one long edge of the cuvette, and the structure printed on the opposite face is typically aligned at an angle, for example 30 degrees, with respect to the long edge of the cuvette.

Fabricating linear gratings on both outside faces could similarly be performed in either of two ways. A master die may be prepared, heated, and the parallel grooves of the linear grating impressed on one outside face of a light-admitting wall of the cuvette. First, one could press grooves into one outside face, rotate the cuvette 180° about its central axis, and impress the same pattern on the opposite outside face. Second, one could make two master heated surfaces and press both groove patterns into the outside faces simultaneously.

In another embodiment of the invention, microcontact printing of periodic structures is done on the inside faces of the cuvette instead of the outside faces.

In another embodiment of the invention, microcontact printing of the aligned gratings is done on opposite faces of one light-admitting wall of the cuvette.

In another embodiment of the invention, the outside of one light-admitting wall of the cuvette is printed, molded, or laminated with a grating structure and the inside of the opposite light-admitting wall is printed, molded, or laminated with a grating structure rotated at an angle to the alignment direction of the outside-formed grating.

In another embodiment of the invention, a transmission grating is printed, molded, or laminated on the outside or inside of one transmitting wall of a cuvette. On either the inside or outside face of the opposite wall, heretofore presumed to be transmitting, a single dispersion or double dispersion diffractive structure is printed, embossed, laminated, or molded onto the face such that light incident through the still-transmitting (but diffracting) wall of the cuvette can reflect and diffract off the reflection grating, returning through the sample solution and rediffracting through the transmission grating. In this embodiment, the light is diffracted a total of three times, twice by the transmission grating on the first wall and once by the reflection grating.

In another embodiment of the invention, transmission gratings are printed, molded, or laminated onto both sides of a transmissive wall of a cuvette, and a reflection grating is laminated, printed, or molded onto one face of the opposite wall. In this case, the incident beam is diffracted up to 5 times before re-emerging in the direction opposite which it entered. In this case, the primary axis of at least one grating does not align with the principal axis of at least one other grating, and 0, 1, 2, or 3 of the gratings have principal axes not aligned with the edge of the cuvette.

In another embodiment of the invention, the cuvette is formed by stacking transparent, refractive rods which are bound together by a transparent binder with refractive index of the binder different than that of the rods at one or more wavelengths. Rods of one diameter, for example 5 micrometers, are stacked to form one transmissive wall of the cuvette and rods of a different diameter, for example 8 micrometers are stacked to form the opposite transmissive wall. The side walls or non-transmissive walls may or may not contain either or both sizes of rod. The stacked rods and spaces in between are then filled with a polymer or hydrogel that solidifies by cooling, polymerization, solvent removal, or cross-linking to form a clear structure with periodically-varying refractive index.

Embodiments of the present invention provide temperature controlled templates on which the desired linear or two dimensional periodic pattern of a grating is embossed or etched, and mechanical assemblies for using such temperature controlled templates to emboss gratings on outside and inside faces of a cuvette. Combinations of the assemblies described herein may emboss gratings on up to four faces of two light-admitting walls of a cuvette.

BRIEF DESCRIPTION OF THE DRAWINGS

FIGS. 1A through 1C illustrate perspective views of cuvettes each with transmission diffraction gratings on opposite walls. FIG. 1D illustrates a top view of a cuvette having a square base.

FIGS. 3, 3A, and 3B illustrate a photolithographically-imposed pattern on silicon for linear or two-dimensional regular structures.

DETAILED DESCRIPTION OF THE INVENTION

Figure 2B:
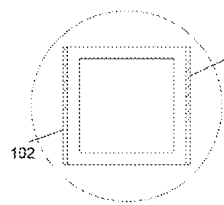
FIGS. 2A through 2H illustrate possible combinations of grating positions in the invention.

Embodiments of the present invention provide a cuvette, a container in which a sample may be placed while the container acts to disperse light as a function of color, wavelength, or frequency. The cuvette/disperser combination is designed in such a way that its properties may be calibrated using appropriate mathematical models for the behavior of the components, thus allowing single use, if desired, or multiple use of the inexpensive container/disperser. Each aspect of the invention is now described individually, and then the combination explained.

Cuvette

According to embodiments of the present invention, a cuvette for specimens being probed for optical absorbance may be a container formed from walls enclosing a well, the walls including at least one light-admitting wall. The walls may include a non-light-admitting wall. A light-admitting wall may be optically flat. A non-light-admitting wall may be non-optically-flat and may be frosted, translucent, opaque, or otherwise non-transparent. Multiple light-admitting walls of a common cuvette may be mutually positioned nearly parallel with well-defined wall separation in construction.

Each light-admitting wall may be positioned to provide a traversal path by which light may traverse the light-admitting wall and the well, rather than through non-light-admitting walls. A cell path length of the cuvette may refer to the distance of light traversal through the well when light traverses a light-admitting wall and the well. According to embodiments of the present invention, a cuvette may have a square base and provide a 1 cm cell path length; examples include a cuvette having a 1 cm by 1 cm base or a 1 cm (across the traversal path) by 1 mm (parallel to the traversal path) base, and having a height of 4.5 cm or 3 cm. Generally, a cuvette may have a square base; a rectangular base; or a cylindrical base where planar light-admitting walls are set at ends of a cylindrical non-light-admitting wall. FIG. 1D illustrates a top view of a cuvette having a square base. A cuvette may have a cell path length of 1 mm, 2 mm, 2.5 mm, 12.5 mm, 1 cm, 2 cm, 10 cm, or may have any other operative path length.

A wall according to embodiments of the present invention may be formed of any material that is transparent at wavelengths relevant to a particular spectrometric measurement and does not react with, or dissolve in, an analyte, solvent, or surrounding atmosphere relevant to the particular spectrometric measurement. According to embodiments of the present invention, walls of a sample holder may be formed from polymers, or from quartz, glass, sodium chloride, sapphire, calcium fluoride, lithium fluoride, or other transparent, insoluble materials. A wall may have an outside face facing the exterior of the cuvette and may have an inside face facing the well of the cuvette.

A light beam may traverse the cuvette by a traversal path from a given incident direction, by which the beam may traverse at least one light-admitting wall and the well, and encounter at least two gratings. The incident direction of the traversal path determines the first grating encountered by the beam and the second grating encountered by the beam.

A cuvette providing a traversal path wherein a first grating encountered by an incident light beam is a transmission grating and a second grating encountered by an incident light beam is another transmission grating is referred to herein as a transmission cuvette; a side of a transmission cuvette facing the incident direction of the traversal path is referred to herein as the incident side; and a side of the cuvette opposite the incident side is referred to herein as the transmission side.

A cuvette providing a traversal path wherein a first grating encountered by an incident light beam is a transmission grating and a second grating encountered by an incident light beam is a reflection grating is referred to herein as a transmission/reflection cuvette; a side of a transmission/reflection cuvette facing the incident direction of the traversal path is referred to herein as the incident side.

FIGS. 1A through 1C illustrate transmission cuvettes according to embodiments of the present invention. FIG. 1A illustrates a cuvette 100 with no tabs, fins, or handles to aid alignment or handling. FIG. 1B illustrates a cuvette 110 with tabs at the top of and contiguous with the outside face of a light-admitting wall of the cuvette, including right hand handling tab 111 (as viewed through incident side of cuvette) and left hand handling tab 112 (as viewed through incident side of cuvette). FIG. 1C illustrates a cuvette 120 with tabs located at the top of and partway along non-light-admitting walls of the cuvette, including right hand handling tab 121 (as viewed through incident side of cuvette), and left hand handling tab 122 (as viewed through incident side of cuvette); such tabs may be located center or off-center along the non-light-admitting walls.

Each cuvette has diffraction grating 101 embossed on the light-admitting wall of the incident side, a diffraction grating 102 embossed on the light-admitting wall of the transmission side, and a main body 103 having inside dimensions typically 1 cm by 1 cm by 4.5 cm, outside walls typically 1 to 2 mm thick.

While one may certainly place a square cuvette in a square holder with the correct orientation, there is a non-vanishing probability that the wrong orientation will be used and the measurement results degraded. Further, fingerprints on the optical faces of the cuvette degrade measurement quality. Having a handle or tab to grab makes handling the cuvette easier, and that tab can be used to orient the cuvette with unambiguous orientation. Thus, embodiments of the present invention further provide cuvettes having built-in handling members, such as orienting tabs or projections, to improve handling ease and guarantee that sample insertion into any instrument is correct.

Handling members according to embodiments of the present invention may be configured as follows. A cuvette of the invention is employed as an element of an instrument as shown in FIGS. 7 and 8. The orientation and alignment of the cuvette with respect to other elements of the instrument set the incidence direction of the traversal path of light upon the cuvette such that the traversal path intersects a detector of the instrument. While a user may manually orient the cuvette to set the incidence direction without tabs, fins, or other appendages to assist such orientation (100), having orienting handling members, such as a tab, is helpful in easing use of the invention.

Examples of handling member orientations are shown in FIG. 1 (110, 120). One example shows a single handling member (111) on the right and a single handling member (121) on the left as viewed from the incident side of a cuvette, of a size and design convenient for handling with a thumb and finger or with a mechanical pincer device as is common in robotics. Another example shows handling members in the centers of non-incident, non-transmission sides of a cuvette (121 and 122). Embodiments of the present invention may provide a single tab among a pair shown herein (say, just 111 or just 112 or just 121 or just 122) for handling and orientation. Embodiments of the present invention may provide tabs on the transmission side of the cuvette (adjacent to items (102) instead of the incident grating (101)) for similar utility. Embodiments of the present invention may provide tabs which interface with mating clips, slots, or other contacting and orienting surfaces in the instrument.

In all cases, the tabs are not illuminated when the cuvette is employed for spectrometry; they are used to aid handling and to aid alignment in the spectrometer. While tabs are not shown on other drawings herein, all tab arrangements may be employed with all designs as convenient.

Gratings

A grating according to embodiments of the present invention may be a periodic structure of regularly spaced rulings, density variations, corrugations, or refractive index variations. A grating may obtain optical spectra from collimated light beams by transmitting a beam through or reflecting a beam from the grating. If the regular spacing is at a separation d and the angle between the normal to the regularly spaced structure and the incoming beam is α, various wavelengths (colors) of light will emerge visibly only where the following relationship holds:

For light beams reflecting from a grating, $$n\lambda = d(\sin(\alpha) + \sin(\beta)) \quad (1)$$

where n is an integer and β is the angle with respect to the normal to the regularly spaced structure of the emergent beam.

For light beams transmitted through a grating, $$n\lambda = d \cos(\theta)\sin(\beta) \quad (2)$$

where variables have their previously described meaning and θ is the rotation of the grating about an axis perpendicular to the periodic property variations.

Gratings according to embodiments of the present invention may be single dispersion gratings, having a periodic structure of parallel rulings, density variations, corrugations, or refractive index variations; or double dispersion gratings, having a periodic structure of two-dimensional patterns of rulings, density variations, corrugation, or refractive index variations.

Reflection and transmission gratings according to embodiments of the present invention may be configured as follows. The invention comprises at least two gratings each at a wall of the cuvette, at least one of which (101, 201, 202, 203) is a transmission grating, and one of which (102, 202) a transmission grating or a reflection grating. Each grating is understood to be a single dispersion grating, a double dispersion grating, or a composite stack of two or more gratings in intimate contact. A grating at a wall of the cuvette may be laid over, or may be integral to, an outside face (101, 102) or inside face (201, 202, 203) of that wall.

Figure 2D:
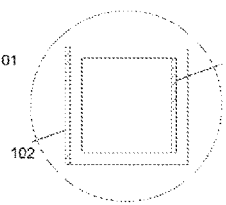
Figure 2F:
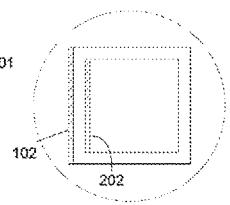
Figure 2H:
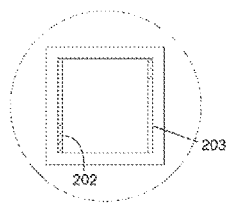
Figure 2A:
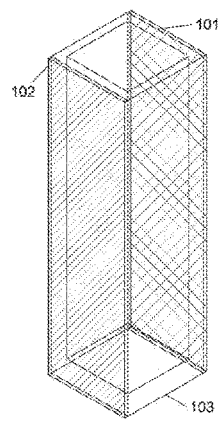
Figure 2C:
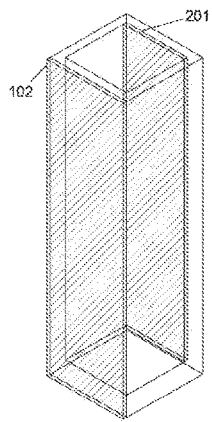
Figure 2E:
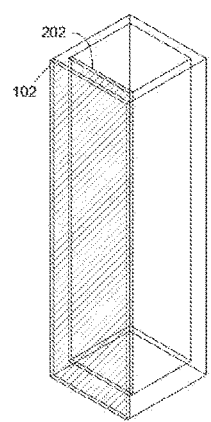
Figure 2G:
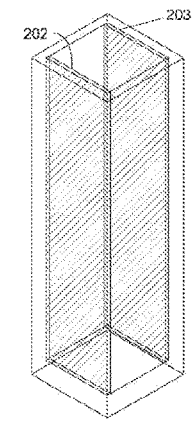

FIGS. 2A through 2H illustrate possible combinations of grating positions in the invention. FIGS. 2A and 2B illustrate an isometric view and a top view, respectively, of a cuvette with gratings on the outside faces of opposite-side walls. FIGS. 2C and 2D illustrate an isometric view and a top view, respectively, of a cuvette where one grating is on an inside face and one grating is on an outside face of opposite-side walls. FIGS. 2E and 2F illustrate an isometric view and a top view, respectively, of a cuvette where both gratings are on opposite faces of the same light-admitting wall. FIGS. 2G and 2H illustrate an isometric view and a top view, respectively, of a cuvette where both gratings are on inside faces of opposite-side light-admitting walls. In all cases, both gratings may be transmission gratings or one may be a transmission grating and the other a reflection grating, with the exception that according to FIGS. 2E and 2F inside face gratings cannot be reflecting, as then light would either never reach the outside face grating (if incident through the opposite-side wall of the cuvette) or would never reach the specimen of interest (if incident through the transmission grating on the outside face and reflecting off the inside face). An exception to this exception is if the inside face grating is sufficiently thin to be partially transmitting so that it could be used to probe a sample e.g. using evanescent waves. In these drawings, 201 denotes a grating on an inside face of a wall that does not also have a grating on its outside face, and 202 denotes a grating on an inside face of a wall that may also have a grating on its outside face.

Orientation of gratings according to embodiments of the present invention may be configured as follows. The orientation of a spectrum depends on the orientation of the grating giving rise to dispersion. Thus, the rotation about an axis normal to one grating, or of one grating with respect to another if there are two or more gratings, in the disclosed invention is critical in giving rise to a predictable, interpretable spectrum.

Typically, the first grating an incident light beam encounters is a transmission grating (101, 102, 201, 203) at a light-admitting wall. If the first grating is a single dispersion grating, the rulings will make some angle θ with respect to the light-admitting wall (if a square or rectangular cuvette geometry is employed, the angle is with respect to a straight edge of the wall; if a cylindrical geometry is employed, the rulings of such a grating would provide a reference orientation or direction). Common orientations are 0°, 30°, 45°, 60°, and 90°, but any angle is acceptable so long as it is known (not unintentionally random). If the first grating is a double dispersion grating, the x axis of the grating (that axis perpendicular to which the most closely spaced diffraction orders are seen, thus for n in equation 1=0, 1, 2, . . . , the apparent value of d is largest) is similarly oriented at 0°, 30°, 45°, 60°, and 90° with respect to the light-admitting wall, but any angle is acceptable so long as it is known (not unintentionally random).

If present, the second grating encountered (102, 201, 202) may be a transmission grating (102, 201) at a light-admitting wall, or may be a reflection grating (202) at a light-admitting wall or at a non-light-admitting wall. The second grating may be a single dispersion grating or may be a double dispersion grating. The angle of the rulings of the second grating with respect to the light-admitting wall may assume any value, but typical values are 0°, 30°, 45°, 60°, and 90°. Commonly, the orientation of the second grating differs from that of the first grating.

Gratings according to embodiments of the present invention may be configured as follows. For a transmission cuvette, the possible combinations are: a first grating on an outside face of a light-admitting wall and a second grating on an outside face of another light-admitting wall (101, 102) as shown in FIGS. 2A and 2B; a first grating on an outside face of a light-admitting wall and a second grating on an inside face of another light-admitting wall (102, 201) as shown in FIGS. 2C and 2D; a first grating on an inside face of a light-admitting wall and a second grating on an outside face of another light-admitting wall (201, 102) as shown in FIGS. 2C and 2D; a first grating and a second grating on opposite sides of a light-admitting wall (102, 202) as shown in FIGS. 2E and 2F; and a first grating on an inside face of a light-admitting wall and a second grating on an inside face of another light-admitting wall (203, 202) as shown in FIGS. 2G and 2H.

Two transmission gratings on opposite faces of same wall: If the wall is on the transmission side of the cuvette, so that all collimated light passes through the sample before reaching the gratings, this geometry produces cylindrically-symmetrical spectra of multiple diffraction orders. However, if the wall is on the incident side of the cuvette, this geometry maximizes the effect of specimen refractive index on spectra. Manufacture of gratings on the inside of the cuvette is more difficult than on the outside walls.

Transmission gratings on outside faces of different walls: this geometry is the easiest to manufacture and the simplest for data interpretation. For light that is diffracted at zero order from the first-encountered grating, refractive index only influences effective path length, not transmission angle. Thus, this geometry allows the simplest iteration of raw data to interpreted spectra with internally-consistent interpretation of refraction effects on both propagation direction and path length.

Reflection grating on outside face of a wall, transmission grating on opposite face of same wall: While suffering from the manufacturing difficulties of two transmission gratings on the same wall, this geometry allows presentation of a sample to a viewing port on a spectrometer instrument rather than requiring that the cuvette be inserted into the instrument, surrounded by other optical components. Such side-on viewing is convenient for rapid measurement and is infeasible with prior technology.

Reflection grating on outside face of a wall, transmission grating on outside face of opposite wall: This geometry is easier to fabricate than the prior one, provides the same advantage for measuring refractive index by successive approximations as the dual outside transmission geometry, and yet allows for presentation of the sample to the instrument without insertion into a cavity in the device, making walk-up measurement simpler and more rapid than other approaches.

For a transmission/reflection cuvette, the possible combinations are: a transmission grating on an outside face of a light-admitting wall and a reflection grating on an outside face of a light-admitting wall (101, 102) as shown in FIGS. 2A and 2B; a transmission grating on an outside face of a light-admitting wall and a reflection grating on an inside face of a light-admitting or non-light-admitting wall (102, 201) as shown in FIGS. 2C and 2D; a transmission grating on an inside face of a light-admitting wall and a reflection grating on an outside face of a light-admitting wall (201, 102) as shown in FIGS. 2C and 2D; a transmission grating on an inside face of a light-admitting wall and a reflection grating on an outside face of the same wall (202, 102) as shown in FIGS. 2E and 2F, and a transmission grating on an inside face of a light-admitting wall and a reflection grating on an inside face of a light-admitting or non-light-admitting wall (203, 202) as shown in FIGS. 2G and 2H. The combination of gratings gives rise to multiple orders whose number and orientation depends on the spacings and rotational orientation of the grating rulings.

The combination of gratings gives rise to multiple orders whose number and orientation depends on the spacings and rotational orientation of the grating periodic patterns. While gratings of essentially identical spacing and orientation (say, all rulings parallel to the longest edge of the cuvette) can be made with the invention, it is most advantageous when each grating is different in spacing, rotation with respect to the longest edge, or pattern (linear vs. two dimensional) with respect to the other or others. For this explanation, take the reference direction as linear rulings parallel to the longest edge of the cuvette. One pair of gratings would have one grating aligned in the reference direction and the other (either on an inside or outside surface) rotated perpendicular to the reference direction. In effect, these two linear gratings would form a two dimensional, double axis grating. Another example would have one grating a double axis grating with a line of indentations or projections aligned in the reference direction, while a second double axis grating is embossed on another of the parallel planar transparent surfaces with a rotation of 30°. Another example would have one grating a linear grating in the reference direction, with a second surface embossed with a double axis grating rotated at 45°. Any combination or linear or double axis grating with any rotation with respect to the reference direction and a total of one, two, three, or four embossed surfaces is an example of the invention.

All drawings attendant to this invention description show gratings covering most or all of the surface or transparent face of each cuvette. While this is one common embodiment of the invention, only that portion of the face through which light from a light source that will reach the detector/camera passes needs to be covered with or imprinted with gratings. In some embodiments, one face is completely covered by grating while one or more others has a smaller region covered by a grating. For example, embossing a region 9 mm in diameter may suffice if the entering beam is 8.5 mm in diameter. Regions not to be embossed with periodic structures are pressed upon by planar regions of the silicon template, or that template is relieved so that the template does not contact the cuvette material during pressing.

While the faces of the cuvette appear to be plane parallel to each other, in fact it is known to experts in the field that the faces are slightly wedged or drafted. Not only does such wedging aid fabrication by providing a means for withdrawing the completed cuvette from a mold, but also such wedging avoids modulation of throughput as a function of wavelength due to the cuvette and its walls acting as Fabry-Perot interferometers. The wedge angle is typically between 0.1° and 2°. Further, the inside and outside faces on each wall of the cuvette may be similarly wedged. Were they not, and if the walls have the most commonly used thickness of 1.25 mm and refractive index of 1.6, throughput would vary with a periodicity of 5 $cm^{-1}$ (with an amplitude dependent on the refractive index of the cuvette contents). Such modulation is undesirable. One attribute of the invention is that templates can pivot so that they are parallel to the planar cuvette wall surface, ensuring uniform embossing over the relevant portion of the surface.

Fabrication

The cuvette must be transparent at the wavelengths of interest for its application. Common materials for visible and near infrared wavelengths include silica-based glasses, quartz, polystyrene, polymethylmethacrylate, and polycarbonate. Because the material is typically amorphous and in many embodiments must soften after the approximate geometry of the cuvette has been molded, thermoplastic materials are preferred over thermosetting materials. Silica-based glasses and quartz present difficulties due to their low coefficient of thermal expansion and high melting point. While it is widely known that linear coefficient of thermal expansion is a function of temperature, typical coefficients for relevant materials are:

Polymethylmethacrylate 73 ppm $K^{-1}$
Polystyrene 70 ppm $K^{-1}$
Polycarbonate 70.2 ppm $K^{-1}$
Silicon 3 ppm $K^{-1}$
Aluminum 22.2 ppm $K^{-1}$
Gold 14.2 ppm $K^{-1}$
Quartz 0.77 to 1.4 ppm $K^{-1}$
Invar 1.5 ppm $K^{-1}$ From these numbers, it is clear that polymers used in cuvettes change dimensions with temperature at a far greater rate than materials used to make molds, templates, or pressure plates. Thus, if a cuvette is in contact with a mold at a temperature T1, it will shrink from that mold if temperature is reduced to a lower temperature T2. For a change of 50° Celsius, a 1.000 mm thick section of a polymer with coefficient of thermal expansion 70 ppm $K^{-1}$ will shrink by 70*50=3500 ppm, 3.5 parts per thousand, or 3.5 micrometers. Each face of the cuvette is expected to retract by 1.75 micrometers. If the depth of impressions in the cuvette face or height of protrusions from that face are less than 1.75 micrometers, the cuvette can be released by the mold or pressure plate and be removed from the forming apparatus without damage. Anticipated embossing depth for gratings and cuvettes useful in the visible region of the electromagnetic spectrum is less than 1 micrometer, showing the needed compliance of cuvette and materials properties.

Indentations or protrusions need to generate a phase shift of light, relative to transit of the cuvette wall through unaltered, planar regions, between 0.2 and 0.8 wavelengths of light for all wavelengths in the observed regions of the spectrum. Considering the range of transparency for typical polymers and the wavelengths detectable with common silicon array detectors, the relevant range of wavelengths is 0.3 micrometers to 1.1 micrometers. Refractive index e.g. for polystyrene is ~1.6 (higher towards the blue, lower towards the red or infrared. Thus 1.1 µm*1.6*0.8=1.4 µm, while 0.3 µm*1.6*0.2=0.1 µm. At the other extreme, 1.1 µm*1.6*0.2=0.35 µm and 0.3 µm*1.6*0.8=0.38 µm. This calculation indicates that the ideal depth or height for modulations in the polymer cuvette surface is 0.35 to 0.4 µm for an air/polymer interface, significantly below the 1.75 micrometer maximum allowable. If the interface is between plastic and water as would be common for inner surface gratings, then the relative refractive index is 1.6/1.33=1.2 and the indentations need to be bigger by 20%=0.42 to 0.48 µm.

A transmission grating according to embodiments of the present invention may be formed from plastic film and may be attached to a face of a wall using adhesives. Adhesive may be applied along the edges of the grating film (so as to be out of the traversal path) or as a thin uniform film fully covering the grating/cuvette interface.

A transmission grating according to embodiments of the present invention may be formed integrally to a wall of a cuvette by a molding process. Typically, a mold is polished to optical smoothness, the cuvette is formed from molten material within the mold, and the mold removed. The surface of a mold may be modulated with indentations or protrusions to form a periodically modulated surface on the optically-transparent walls or faces of the cuvette. In consequence, either single dispersion or double dispersion gratings are molded as part of the cuvette walls, inseparable from the cuvette. The form of these indentations and protrusions is such that the mold can be removed without abrading or otherwise damaging the indentations or protrusions.

A transmission grating according to embodiments of the present invention may be formed from microcontact printing upon a layer of additive material. A periodic structure may be molded onto a layer of material overlaying a face of a wall of the cuvette. For example, polydimethylsiloxane can be formed from monomer in situ with a mold that is the complement to the desired grating structure used to displace the liquid monomer and polymerization catalyst.

A transmission grating according to embodiments of the present invention may be formed from post-molding thermoforming of a face of a wall of the cuvette. A heated form, bearing the negative of the desired grating shape, may be pressed against each wall face and, if the cuvette is made of thermoplastic or similar material, the grating melted or flowed into the face after the cuvette is formed.

A transmission grating according to embodiments of the present invention may be a volume grating formed from two-component fabrication. A light-admitting wall of a cuvette may be composed of uniform polymer cylinders held in place by a compatible polymer of different refractive index. The cylinders have diameters of the order of the wavelength of light to be diffracted, i.e. 0.5 micrometers to 25 micrometers. Stacking uniform cylinders gives rise to rows of cylinders which, viewed axially, appear to form hexagonally closest packed piles. Intercalated into the stack is a polymer to fill the tricuspid interstitial spaces between the cylinders and to bind the array into a stable solid. Either one wall or both opposite walls of the cuvette may be so formed. In the case where only one wall is formed as a stacked polymer rod grating, the grating on the opposite wall may be formed by any of the other methods herein described.

A transmission grating according to embodiments of the present invention may be formed by photolithographic injection-molding on cuvette surfaces. A means to this end is:
1) Make an injection mold for a cuvette in the way commonly practiced.
2) Highly polish those surfaces that will form the optically transparent windows.
3) Cover said mold surface with a photoresist.
4) Photopolymerize said photoresist except where lines, impressions, or other periodic structures are desired in the mold. Rinse away unpolymerized photoresist.
5) Using an etchant appropriate to the mold material, etch lines or hemispheres or other desirable intrusions into the mold that will form corresponding extrusions on the surface of the molded cuvette.
6) After an appropriate time, rinse the etchant from the mold.

The mold can now produce a grating that is an integral part of the face of the cuvette, angled appropriately if the photolithography was properly performed, provided the polymer flows into the micron-scale surface modulations. This may require that injection molding be done in vacuum.

A reflection grating according to embodiments of the present invention may be formed by conversion from a transmission grating. The geometric form of reflection gratings is the same as the form of transmission gratings made with some type of surface relief (as opposed to having uniform geometry with modulated refractive index). To turn a transmission grating into a reflection grating, a uniform metallization of the modulated surface is required. Vapor deposition of aluminum and electroless deposition of silver using Tolens Reagent are known methods for metallization.

Embodiments of the present invention provide temperature controlled templates on which the desired linear or two dimensional periodic pattern is embossed or etched, depending on whether a depressed or elevated periodic pattern in the grating/cuvette combination is desired. First, a master pattern is created by well-known means of microfabrication such as photolithography, electron beam etching, electrodeposition, or chemical etching. The master pattern may be made on a substrate whose coefficient of thermal expansion is known as a function of temperature, whose softening or glass transition temperature is at least 50° C. higher than the softening or glass transition temperature for the cuvette material, and whose grain structure is smaller by a factor of at least 3 and preferable by a factor of 10 compared to the features to be embossed. Second, the master is mounted on a metal or thermally conductive ceramic block whose temperature can be controlled at will, preferably electronically but optionally by inductive heating or through flow of a thermostated liquid. Third, the dimensions and angles of the cuvette, masters and mounting blocks must be chosen as described herein to allow intimate contact between the master surfaces and the cuvette while facilitating dig and scratch free movement of the cuvette onto and off of the master/block combination. Fourth, a preformed, non-embossed or non-pressed cuvette is provided to the disclosed apparatus. The block or blocks holding the master or masters is heated to a temperature below the glass transition temperature of the bulk polymer of which the cuvette is composed, but above the softening temperature of the polymer when it is subjected to compressive forces. Fifth, the master or masters are pressed onto the face or faces of at least one base wall of the cuvette, and the pattern is embossed or pressed into the face or faces. The block is cooled below the softening temperature, after which pressure is released. The coefficient of thermal expansion of the master and block is chosen to be less than the coefficient of thermal expansion of the cuvette, facilitating freeing of the cuvette from the templates and mold. After the cuvette is removed from the embossing/pressing mold, the process may be repeated. The disclosed invention applies whether embossing is done one grating at a time or embossing multiple faces simultaneously.

For the purpose of this specification, "base wall" shall refer to a wall of a cuvette wherein a grating is embossed upon at least one face of the wall. "Non-base wall" shall refer to a wall of a cuvette where no gratings are embossed upon any faces of the wall.

In one embodiment of the invention, a grating is impressed on an outside face of a light-admitting base wall of a cuvette made of polystyrene of otherwise conventional design. One polished planar surface of a silicon wafer of arbitrary thickness but preferably between 0.1 mm and 1 mm is etched using photolithography of conventional nature such that the surface has grooves of width 1 micrometer, depth 0.45 micrometers, spaced on 5 micrometer centers, with the grooves extending a distance of 50 mm while the cuvette has a height of 45 mm, thus having the grooves in the silicon longer than the cuvette. The number of parallel grooves in the silicon is greater than 2500, since the cuvette has a width of 12.5 mm so that at least 2500 grooves are needed to completely cover the face of a light-admitting base wall of the cuvette. The silicon wafer is set, unetched side down, on a planar surface maintained at a temperature of 85° C. The cuvette is coated with a thin layer of releasing agent such as a low viscosity silicone oil. The long edge of the cuvette is aligned with the grooves in the silicon, the cuvette is heated to 85° C., and one face of a light-admitting base wall of the cuvette is pressed against the grooved region of the silicon wafer with a force of 1.8 to 2 megapascals, approximately 18 to 20 atmospheres. This is preferably achieved by placing a polished metallic block on the clear face opposite the face into which grooves are being pressed, allowing the cuvette to be forced into the grooves in the silicon template facing the opposite side of the cuvette. Pressure can be generated with masses or hydraulic pressure mimicking such mass putting a total mass of 27 kg on the strips, thus uniformly loading the 5.625 square centimeter face of a light-admitting base wall of the cuvette with the desired loading. After a suitable period, of the order of one second, pressure is removed and the cuvette, wafer, and supporting surfaces cooled sufficiently for the cuvette to shrink from the molding surface, in the range of 20° C. to 40° C. A grating with grooves parallel to the cuvette edge will be embedded in the face of the cuvette previously in contact with the silicon wafer. The grating will have protrusions extending from an otherwise planar surface.

In another embodiment of the invention, gratings are impressed on the outside faces of a first and a second light-admitting base wall of a cuvette made of polystyrene of otherwise conventional design. One polished planar surface of a silicon wafer of arbitrary thickness but preferably between 0.1 mm and 1 mm is etched using photolithography of conventional nature such that the surface has grooves of width 1 micrometer, depth 0.45 micrometers, spaced on 5 micrometer centers, with the grooves extending a distance of 50 mm while the cuvette has a height of 45 mm, thus having the grooves in the silicon longer than the cuvette. The number of parallel grooves in the silicon is greater than 2500, since the cuvette has a width of 12.5 mm so that at least 2500 grooves are needed to completely cover the face of a first light-admitting base wall of the cuvette. A second silicon wafer is similarly etched, though not necessarily with the same groove spacing. Further, the number of etched grooves may differ from that of the first wafer. For this embodiment, the second wafer is employed to emboss a grating on a second light-admitting base wall on the opposite side of the cuvette from the first light-admitting base wall as described in the first embodiment, and the grooves are rotated such that the etched grooves make an angle of 45° with respect to those of the first wafer. To ensure complete coverage of the face of the cuvette, the number of etched lines must be increased by a factor of the square root of 2 meaning 2500*1.4142=3536 grooves are required, and several additional grooves, for example a total of 3600 grooves, simplify alignment of the grating-bearing cuvette. The first silicon wafer, unetched side facing down, is set on a planar surface maintained at a temperature of 85° C. The cuvette is coated with a thin layer of releasing agent such as a low viscosity silicone oil. The long edge of the cuvette is aligned with the grooves in the silicon. The second silicon wafer, grooved side facing down (towards the cuvette) is rotated at the desired 45° angle about an axis perpendicular to the grooves and to the plane of the grooves and set on the cuvette. The cuvette is heated to 85° C., and the stack of heated surface, first wafer, cuvette, and second wafer, also heated to 85° C., is pressed together with a force of 1.8 to 2 megapascals, approximately 8 to 10 atmospheres. This is preferably achieved by applying masses or hydraulic pressure mimicking such mass putting a total mass of 27 kg on the component stack, thus uniformly loading the 5.625 square centimeter face of light-admitting walls of the cuvette with the desired loading. After a suitable period, of the order of one second, pressure is removed and the cuvette, wafers, and supporting surfaces cooled sufficiently for the cuvette to shrink from the molding surface, in the range of 20° C. to 40° C. A grating with grooves parallel to the cuvette edge will be embedded in the outside face of a first base wall of the cuvette previously in contact with the lower silicon wafer, and a grating with grooves rotated 45° with respect to the cuvette edge will be embedded in the outside face of the second, opposite-side base wall. The gratings will have protrusions extending from an otherwise planar surface.

In another embodiment of the invention, gratings are embossed on the inside and outside of a light-admitting base wall of a cuvette. A four part assembly of low expansion material such as steel or aluminum is machined such that one component is the same size as the inside face of a non-base wall of the cuvette and between 1 and 3 millimeters thick, a second component is of similar size but with a track on the side, facing the inside face of the opposite-side light-admitting base wall of the cuvette, into which a silicon template may slide, sandwiching a flexible polymer (rubber, silicone rubber, or polyamide) gasket admitting a thermostating fluid such as water, ethylene glycol, mixtures of water and ethylene glycol, or other noncorrosive liquids that remain fluid between 1° C. and 99° C. A silicon wafer with etched grooves in the manner of previously described embodiments is inserted into the tracks on the face of the second component and placed in contact with the inside face of a light-admitting base wall of the cuvette. This combination is set on a grooved template in the manner described in the first embodiment. A thermostated block supports the outer grooved template on which sits the cuvette inside of which sits the second grooved template, metal support, gasket, and rear metal block. In this instance, a polished pressure plate covering the entire exposed transparent rear face of the cuvette is placed over the top surface of the cuvette press assembly. The assembly is heated to 85° C. The gasket is then inflated to a pressure of 2 megapascals. The top pressure block is also pressed against the assembly with a pressure of 2 megapascals. In consequence, grooves are pressed into the inside and outside faces of a light-admitting base wall of the cuvette while planar surfaces yield no deformation to the opposite-side non-base wall. After approximately one second, pressure is reduced, after which temperature is reduced to between 15° C. and 40° C. The central metal/gasket/metal/template component is withdrawn from the cuvette, the top pressure plate removed, and the cuvette now has grating grooves on both faces of one light-admitting base wall.

In another embodiment, the formation methods are as described in the prior embodiments except that one or more of the silicon templates are etched with a regular pattern of holes about one micrometer in diameter in an otherwise planar surfaces, the holes spaced at a regular, rectilinear distance of about five micrometers, thus allowing pressing of double axis gratings. Further, the pattern may be arbitrarily rotated as suggested by U.S. Pat. No. 8,885,161 so that the regular patterns of the two dimensional grid may be registered at a controlled angle with respect to the other template (internal or external to the cuvette).

In another embodiment of the invention, a grating is formed on the outside face of a first light-admitting base wall of the cuvette and on the inside face of a second, opposite-side light-admitting base wall of the cuvette. Geometry for the externally formed grating is as was described in the first embodiment. Geometry for the opposite, external side is a polished flat metal block to uniformly cover the exposed surface. The plug insert is as described in the previous embodiment where one side is a flat metal plate fully covering an inside face of the first base wall of the cuvette which is not to be imprinted with a grating, the other of which has mounting tracks to support an etched silicon grating master. The two metal pieces sandwich a flexible polymer gasket. Silicon wafer templates are etched as in prior embodiments. From bottom to top, there is a thermostated block; the first silicon etched template; and the cuvette, inside of which is the assembly of two metal pieces, one with silicon template facing up, the other with a smooth surface facing down, between which is the flexible polymer gasket through which thermostated fluid can flow. On the top is a flat metal pressure plate. The assembly is heated to 85° C. Simultaneously, the outer plates are forced together with a pressure of 2 megapascal and the gasket is inflated so that the internal faces of the plug exert a pressure of 2 megapascal. After approximately one second, pressure is reduced, the assembly is cooled to between 20° C. and 40° C., the central plug is removed and the silicon wafer/cuvette sandwich disassembled. One outside face of the cuvette has an embossed grating, while the opposite inside face has an embossed grating.

Figure 3:
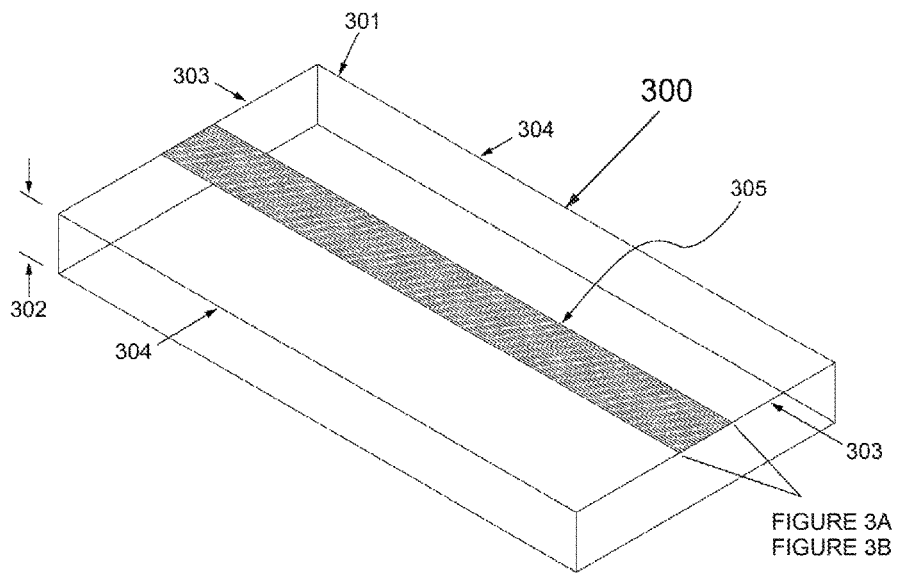
Figure 3:
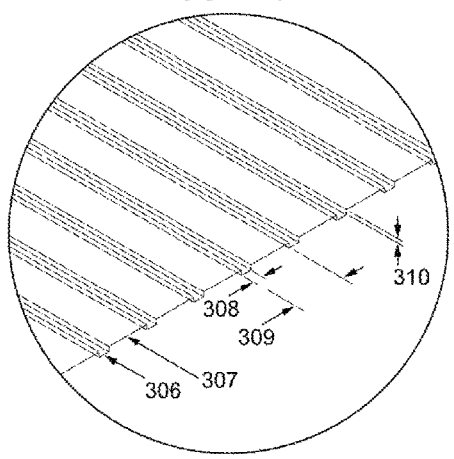
Figure 3:
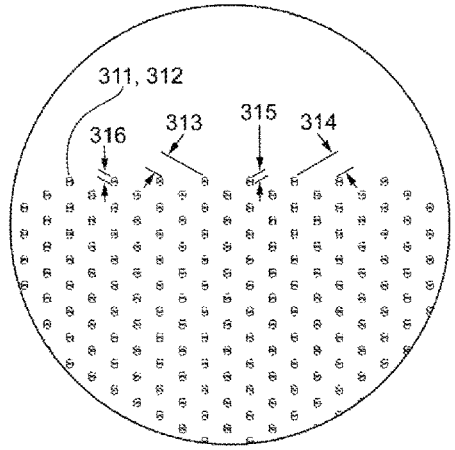

FIG. 3 illustrates a photolithographically-imposed pattern on Si(111) for linear or two-dimensional regular structures. A silicon template with etched surface 300 is formed by silicon substrate 301, having a thickness 302 of typically 0.1 to 1 mm; having a length 303 of typically the height of the cuvette if used on the outside surface, or the depth of the cuvette if used on the inside surface; and having a width 304 typically 2 to 20 mm wider than the transparent face of the cuvette for impressing gratings on an outside face of a wall of a cuvette, or typically 0.1 to 0.5 mm narrower than the transparent face of the cuvette for impressing gratings on an inside face of a wall of a cuvette.

FIGS. 3A and 3B illustrate the etched surface 305 of the substrate 301 depending on the nature of gratings to be impressed using the substrate 301. FIG. 3A illustrates a magnified view of silicon substrate 301 for periodic, linear gratings. Etched grooves 306 are separated by unetched, planar silicon 307 between pairs of etched grooves 306. Grooves 306 have width 308 typically ⅒th to ½ of the groove spacing; spacing 309 typically between 100 nm and 20 micrometers; and depth 310 typically chosen so that cuvette polymer refractive index times light vacuum wavelength is between 0.2 times groove depth and 0.8 times groove depth over the range of wavelengths to be employed in conjunction with the formed cuvette.

Grooves 306 are parallel to the edge of the silicon substrate 301 and, thus, typically also parallel to the longest axis of the cuvette. However, grooves 306 may make any angle to the long axis of the cuvette, as desired by practitioners of the invention. Commonly, no two gratings embossed on a single cuvette will have the same alignment with respect to the longest axis of the cuvette.

FIG. 3B illustrates a magnified view of silicon substrate 301 for periodic, double axis gratings, where the substrate 301 has features which are either blind holes 311 or pillars 312. For gratings embossed on the outside of cuvettes, blind holes 311 extend into the silicon substrate so that corresponding bumps protrude from the cuvette surface; for gratings embossed on the inside of cuvettes, pillars 312 extend above the etched silicon plane so that indentations project into the clear plastic wall after the grating is embossed on the cuvette. Features, either blind holes 311 or pillars 312, are separated by column spacing 313, typically 100 nm to 20 micrometers; and row spacing 314, typically though not necessarily the same as column spacing. Rows and columns are typically, though not necessarily, perpendicular to each other. Rows may parallel the longest axis of the cuvette during embossing, but can be aligned at any angle. Commonly, no two embossed faces will have the same angle between rows and the edge of the cuvette.

Features have a vertical dimension 315 that is either depth for blind holes 311 or height for pillars 312. The vertical dimension 315 is typically chosen so that cuvette polymer refractive index times light vacuum wavelength is between 0.2 times and 0.8 times vertical dimension 315 over the range of wavelengths to be employed in conjunction with the formed cuvette.

Figure 4:
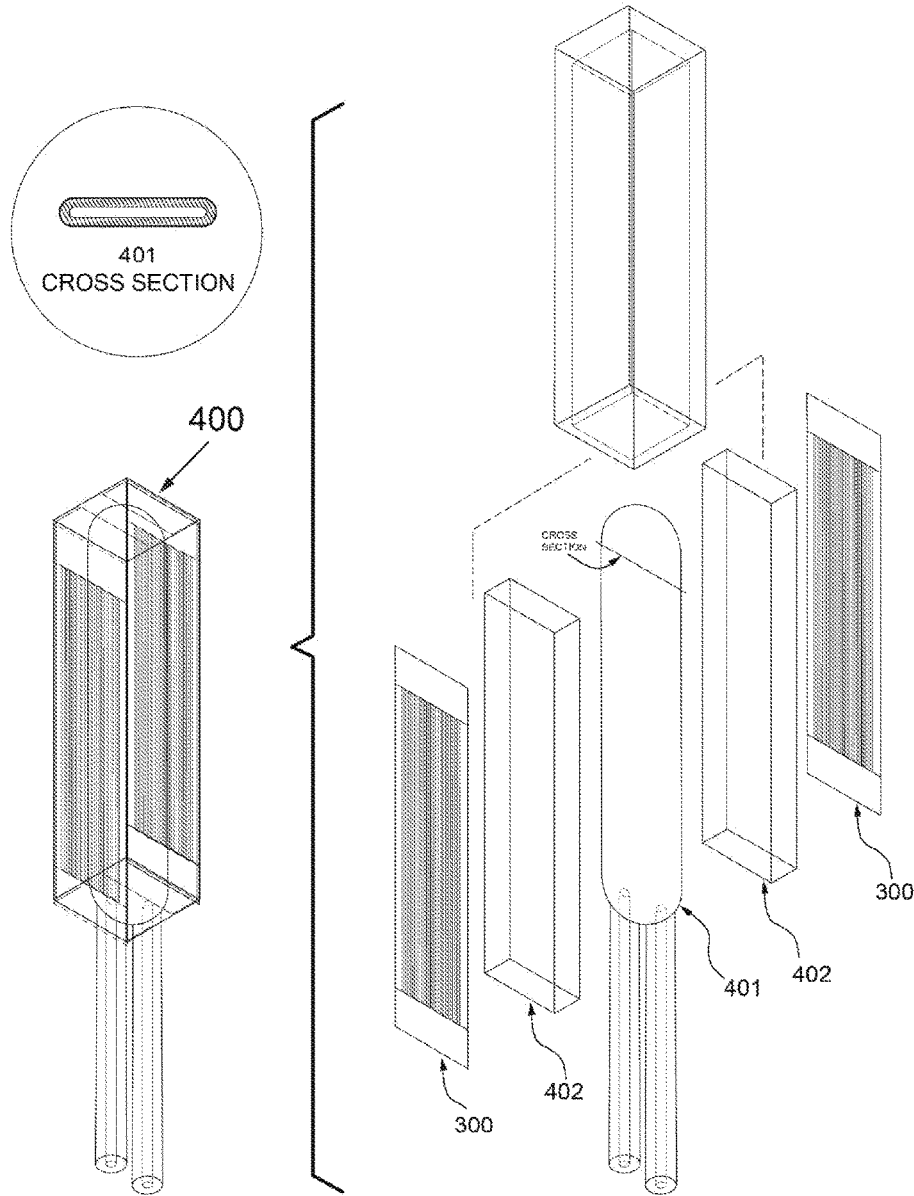
FIG. 4 illustrates an assembly for embossing gratings on the inside faces of walls of a cuvette.

FIG. 4 illustrates an assembly 400 for embossing gratings on the inside walls of a cuvette. The perspective view illustrates the interior chamber of a cuvette, with the assembly 400 components inside. The exploded view illustrates that the assembly 400 includes two silicon templates with etched surface 300, each bearing etched mirror images of the grating pattern with etched surfaces 305 facing the light-admitting cuvette walls; inflatable bladder 401; and two metal inserts 402.

Thermostated fluid may circulate through inflatable bladder 401, which may be pressurized to force silicon templates 300 into the transparent walls. The inflatable bladder 401 may be formed from a flexible polymer such as polydimethylsiloxane, rubber, or other material with glass transition temperature below room temperature (15° C.) and melting, structural weakening, outgassing, or other decompositional temperature above the melting point of the plastic of which the cuvette is composed.

Metal inserts 402 uniformly support silicon templates 300 and transmit force from inflatable bladder 401 to press silicon templates 300 against the inside faces of the cuvette.

Figure 5:
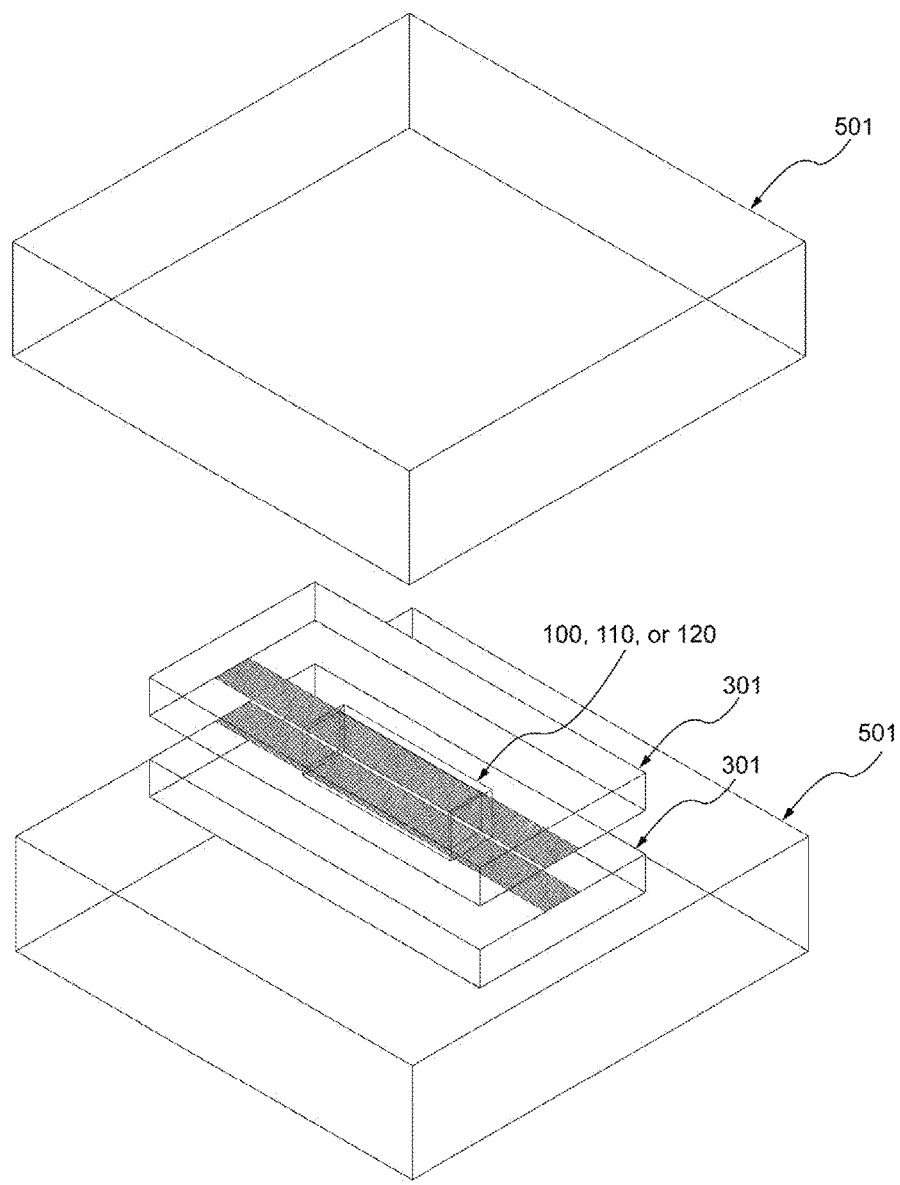
FIG. 5 illustrates an assembly for embossing gratings on the outside faces of walls of a cuvette.

FIG. 5 illustrates an assembly for embossing gratings on the outside faces of a cuvette. The assembly is a stack including a metallic thermostated block 501 sitting on a solid, immobile surface, on top of which sit a silicon template 300, the cuvette to be imprinted (100, 110, or 120), above which sits either a second silicon template 300 (if the outside face of the upper light-admitting wall is to have a grating embossed) or a flat, unembossed silicon blank, above which sits another thermostated block 501. The entire stack is placed in a press (not shown) that can apply the desired pressure for the desired period of time.

Figure 6:
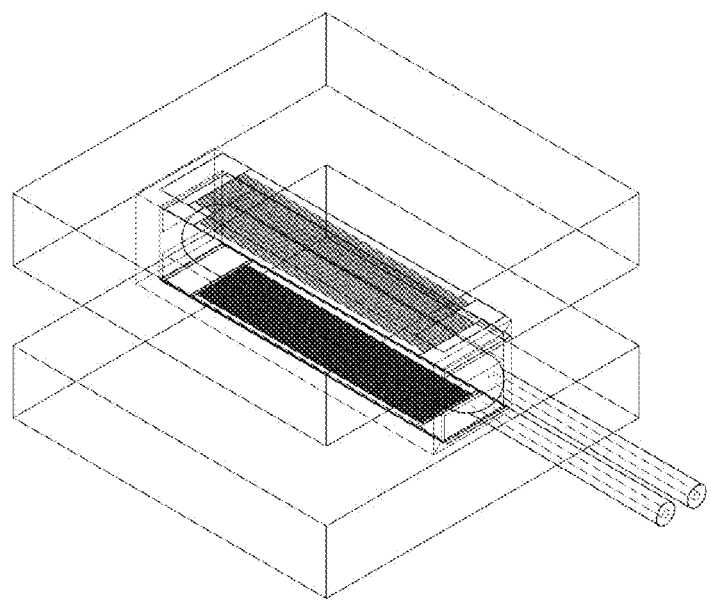
FIG. 6 illustrates a combination of the assemblies of FIGS. 4 and 5.

FIG. 6 illustrates a combination of the assemblies of FIG. 4 and FIG. 5 for embossing gratings on inside and outside faces of the walls of a cuvette simultaneously. Up to 4 faces of two light-admitting walls of a cuvette may be embossed simultaneously.

Photolithography of silicon wafers is a well-established art. Dimensions of desired grooves, protrusions, indentations, and mesas for making gratings with, for example, 300 lines per millimeter, 500 lines per millimeter, 600 lines per millimeter, 1200 lines per millimeter or 2400 lines per millimeter are well known. Dimensions for forming double axis gratings with, for example, 100 mesas per linear millimeter along two perpendicular axes, 200 mesas per linear millimeter along two perpendicular axes, and so on are also well known. Computer assisted drawing programs are used to generate photolithography masters, positive and negative photoresists are employed to protect or expose relevant regions of a planar silicon wafer, and acidic, basic, and fluorinated etchants can be employed to remove silicon in the desired pattern to the desired depth. Thus, forming the master silicon templates is not novel.

Presses and fluid handling must allow for careful control) (±0.5° of temperature and adequate control of pressure (ambient to 5 megapascal, with typical optimum at 2 megapascal). Liquid circulation baths, process controllers, and pressure controllers are common so that widely available components are applied to the invention. To obtain rapid temperature changes, different reservoirs at desired temperatures can supply circulating fluid to the template supports. Valves such as solenoid values may switch liquid flow from a warm (e.g. 85° C.) bath to a cool (e.g. 20° C.) bath under switched control.

Inflatable bladder 401 is a flexible polymer balloon with two feed/exhaust tubes. Liquid or gas circulated in this bladder at pressures less than 1 megapascal are used to bring the surrounding materials to a desired temperature. Pressurized to 2 megapascal, the bladder forces templates into the inside faces of light-admitting walls of the cuvette. At the start of compression, only those areas of the template that extend above the surrounding material contact the polymer, thus placing loads in excess of the deformation pressure on the surface. The mold presses into the surface until the entire template is in contact with the cuvette face. Because of the increased contact surface area, the pressure drops, and by judicious optimization of the pressure and temperature employed, the surface solidifies with the template pattern impressed on that cuvette face. The pressure in the bladder may then be decreased, ensuring that no further penetration occurs. As previously explained, lowering assembly temperature, both by circulating cool fluid through the bladder and through other assembly components, promotes retraction of the cuvette polymer from the mold material, allowing the templating assembly to be retracted and the molded cuvette to be employed.

Combinations of the assemblies described herein may emboss gratings on up to four faces of two light-admitting walls of a cuvette. In cases where fewer gratings are desired, the embossing silicon template adjacent to that face is replaced with an optically flat silicon template (either natively, polished, or etched flat). The assembly starts with a hard, stable surface that forms the lower jaw of a press. On top of this surface is placed a temperature control block, a metal block through which thermostated fluid may circulate. The top surface of this block optionally includes alignment pins or bars to assist positioning of other components. Next, the template used to emboss the first outside surface of the cuvette is positioned on the block surface, above which is positioned the cuvette to be embossed. Inserted into the cuvette is a stack of five components, in order from bottom to top: template for forming the topography of the lower inside wall of the cuvette, metal block approximately 3.5 mm thick (for a 1 cm thick cuvette) to press on the template, the inflatable bladder 401, nominally 3 mm thick, a second 3.5 mm thick metal block, and a second template. For these internal templates, the modulated face presses against the cuvette material, while the unetched, planar side rests against the metal block. Above the cuvette is placed the final template, modulated side facing the cuvette. Above this is placed another thermostated block, onto which the ram of the pressure apparatus pushes. Best practice adds air circulation of thermostated gas at the same temperature as desired of the forming cuvette and as is circulated in the temperature control blocks and pressure control bladder. To confirm when the system reaches equilibrium, it is desirable to have a temperature sensing element such as a thermocouple, thermistor, or infrared camera in contact with, in the vicinity of, or observing the templating stack.

Grating Modulations

Spacing of grating modulations (alternately referred to as lines, rulings, or grooves) according to embodiments of the present invention may be configured as follows. Typical grating periodicity is from 50 rulings per millimeter to 5000 rulings per millimeter. Grating periodicity according to embodiments of the present invention may, for example, be 200 modulations/mm, but may range over a coarse boundary of approximately 100 modulations/mm to a fine boundary of approximately 500 modulations/mm. At spacings greater than 500 modulations/mm, diffraction angles are too large to work with any detectors but ultra-wide field cameras.

It is known that the best relative resolution ($\lambda/\Delta\lambda$) one can obtain from a diffraction grating is nN, where n is the order number in equation 1 and N is the number of rulings, corrugations, or other modulations encountered by the collimated beam. For a single dispersion grating with 500 grooves per millimeter, the resolution ($\lambda/\Delta\lambda$) obtainable in first order from a 5 mm diameter beam is 2500 (i.e. at 500 nm, a resolution of 0.2 nm). These same relationships hold for the multigrating cuvette of the current invention, with the modification that n may not be an integer and is dependent on the net diffraction from all surfaces encountered.

Effect of Sample Refractive Index

Refractive index has two influences on light incident on the cuvette: 1) effective optical path length is proportional to sample refractive index and 2) angle of propagation is a function of refractive index. If light propagates at zero order, only the first of these is significant, as the off-axis angle of the cuvette walls is sufficiently small that refractive dispersion is negligible and all wavelengths follow a common path. Water has a wavelength-dependent refractive index (Daimon, M., & Masumura, A. (2007). Measurement of the Refractive Index of Distilled Water from the Near-infrared Region to the Ultraviolet Region. *Appl. Opt.*, 46(18), 3811-3820.), as do essentially all materials, so for any measurement "path length" is understood to mean "physical distance times refractive index at the wavelength observed."

Changes in refractive index with concentration are a source of calibration non-linearity understood at least as long ago as 1939 (Kortüm, G., & Seiler, M. (1939). Über physikalische Methoden im chemischen Laboratorium. XLI. Die kritische Auswahl colorimetrischer, spektralphotometrischer and spektrographischer Methoden zur Absorptionsmessung. *Angewandte Chemie*, 52(48), 687-693. doi: 10.1002/ange.19390524802, specifically P. 688, column 1, line 5). However, if light is diffracted in non-zero order by the first (transmission) grating, incidence angle on the sample is non-zero, so that different wavelengths will be propagated at different angles. Since refractive index is a function not only of solvent but also of analyte concentration, the dispersion becomes concentration-dependent through the Kramers-Kroenig relationship (Davis, B. J., Carney, P. S., & Bhargava, R. (2010). Theory of Midinfrared Absorption Microspectroscopy: I. Homogeneous Samples. *Analytical Chemistry*, 82(9), 3474-3486. doi:10.1021/ac902067p).

Spectral interpretation thus becomes an iterative process. First, one assumes refractive index is due only to solvent. Pathlength through the sample as a function of order and wavelength is computed, leading to an initial estimate of sample concentration from Beer's Law. The Kramers-Kronig relationships are then used to modify the estimate of refractive index as a function of concentration (a small effect at low concentration, but not at high concentration), and calculations iterated to convergence. The deviation of raw data from pure cylindrical symmetry indicates the influence of refractive index, provides real-time measurement of said index, and provides sample by sample compensation for changes in index.

Wavelength Calibration, Order-by-Order Data Processing

With dual gratings, every observed order can be labeled by the diffraction order numbers corresponding to each of the gratings. The grating equation, $n\lambda = d(\sin\alpha + \sin\beta)$ or $n\lambda = d(\cos\theta \sin\beta)$ applies.

For the case of $n\lambda = d(\sin\alpha + \sin\beta)$, if double-dispersion gratings are used, then d depends on n in the horizontal direction ($n_x$), d in the horizontal direction ($d_x$) and in the vertical direction ($n_y$, $d_y$) such that the effective value of d, $d_{eff}$, is given by $$d_{eff} = \frac{1}{\sqrt{\left(\frac{n_x}{d_x}\right)^2 + \left(\frac{n_y}{d_y}\right)^2}}$$

with n=1 so long as $n_x \neq 0$ or $n_y \neq 0$. For multiple gratings, the value of $\alpha$ at the second grating is the negative of the value of $\beta$ at the first grating. In the current invention, with some geometries, $\beta$ is also a function of refractive index if $\alpha$ is non-zero. If diffraction occurs in a medium with refractive index=1, then the dispersion is known to those familiar with gratings as $$\frac{d\lambda}{d\beta} = \frac{d_{eff}\cos\beta}{f}$$

where n=1 has been employed. If refractive index at the wavelength does not equal 1, then from Snell's Law, using r as the symbol for refractive index (to avoid confusion with diffraction order, a problem in much of the optics literature) $r_1(\lambda)\sin\alpha(\lambda) = r_2(\lambda)\sin\beta_{nodiffraction}$ so that $$\frac{d\beta}{d\lambda} = \frac{d\sin^{-1}((r_1/r_2)\sin\alpha)}{d\lambda} = \frac{1}{\sqrt{1-\left(\frac{r_1}{r_2}\right)^2\sin^2\alpha}}\left(\sin\alpha\frac{d(r_1/r_2)}{d\lambda} + (r_1/r_2)\cos\alpha\frac{d\alpha}{d\lambda}\right)$$

The first term inside the parentheses depends primarily on sample properties. The second term depends on the n's of the first grating. Overall, $d\beta/d\lambda$ is the sum of the refractive and diffractive dispersion. Similar considerations apply to purely transmitting grating systems in the case of $n\lambda = d(\cos\theta \sin\beta)$.

Initial wavelength calibration of an embodiment of the current invention ignores the refractive contribution to dispersion, resulting in order-dependent approximations to $\alpha$. One then includes the influence of refractive index of distilled water and refines the calibration. Where there are alignment discrepancies, such misalignments must be due to sample-dependent refraction, and the first term inside the parentheses becomes important. Using the mathematical technique of successive approximations, widely known to practicing analytical chemists and also known as iterative convergence to a fixed point by mathematicians and physicists, one arrives at an internally-consistent calibration that depends on sample composition and so much be obtained for each specimen.

Design of Spectrometer Using Transmission Cuvette

A square cuvette can be placed in a square hole with one of 4 rotations. For transmission cuvettes of the invention, the gratings need to be oriented in only one way. If there is a reflecting face, that face must not be interposed between incident light and the sample. If there are transmitting faces, and gratings are rotated on one face differently than on another (as is typically the case), then instrument calibration depends on which face is used for light entry, the opposite face being used for light exit.

Figure 7A:
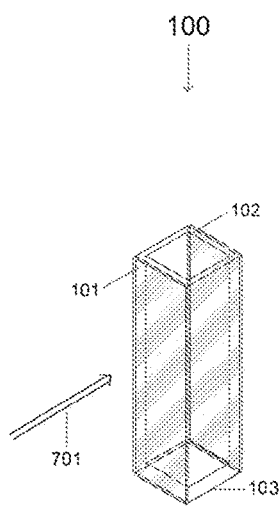
FIGS. 7A, 7B, and 7C illustrate a transmission geometry spectrometer layout.
Figure 7B:
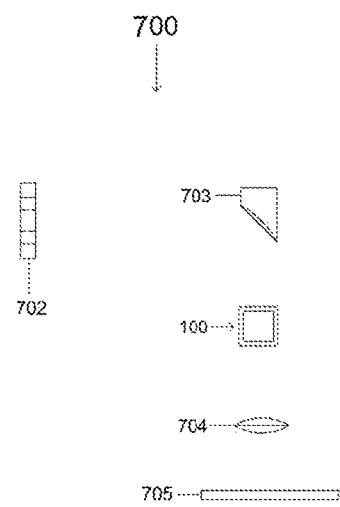
Figure 7C:
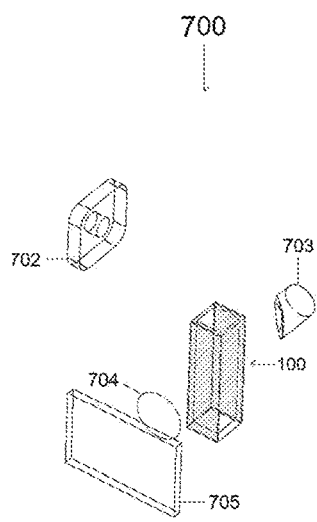

FIGS. 7A, 7B, and 7C illustrate the use of a cuvette of the invention employed in a transmission spectrometer 700, for example used to measure optical absorption. Any of the geometries shown in FIG. 2 that involve two transmission gratings may be used interchangeably. FIG. 7A illustrate san isometric view, FIG. 7B illustrates a top view, and FIG. 7C illustrates an example of the cuvette employed in FIGS. 7A and 7B. Light enters through a pinhole, is collimated with an off-axis parabolic mirror or other collimating optic (perhaps a lens, in which case the assembly could be linear instead of folded), traverses a dual-grating-equipped cuvette of the invention, and then light is focused by a lens onto an observation plane, preferably equipped with an array detector such as a CMOS camera array or CCD array.

FIG. 7A illustrates a case in which an embodiment based on FIG. 2A and FIG. 2B is employed, with the incident side of the cuvette defined by the direction of incident collimated light 701. Absorption path length is the thickness of the cuvette as measured along the traversal path times the refractive index of the liquid in the cuvette, as is commonly understood by those expert in the field. There is an additional variation in path length through the cuvette if diffraction is in other than zero order at the first grating 101. If the diffraction angle is 5°, then the effective path length for that order is the thickness of the cuvette times refractive index divided by cosine (5°).

The cuvette, with either a reference solution or a solution whose spectrum is to be determined, is inserted into a spectrometer seen in top view (FIG. 7B) or in perspective view (FIG. 7C). Light from a suitable source (fiber optic, arc lamp, light emitting diode, incandescent bulb, laser, or other source) enters through a limiting aperture 702, typically a circular pinhole of diameter between 1 micrometer and 1 millimeter. Light is then collimated with a mirror or lens, here shown as an off-axis parabolic mirror 703. The collimated light then traverses a cuvette according to the present invention. The transmitted light is focused by a mirror or lens, here shown as a lens 704 and is detected with a detector, typically a charge coupled array detector (CCD), CMOS detector, or other electronic camera 705. The appearance of the multiple diffraction orders is approximately cylindrically-symmetrical.

Design of Spectrometer Using Transmission/Reflection Cuvette

Figure 8A:
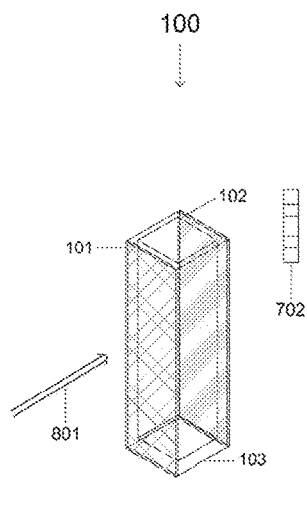
FIGS. 8A, 8B, and 8C illustrate a reflection geometry spectrometer layout.
Figure 8B:
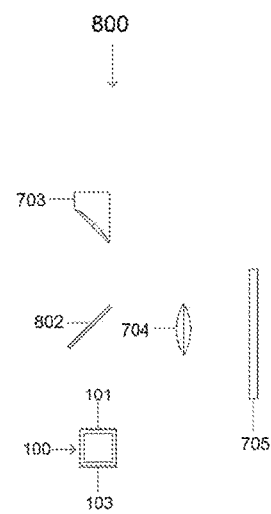
Figure 8C:
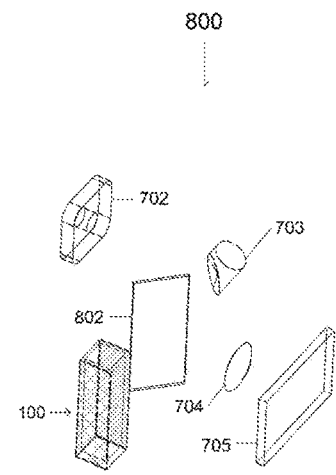

FIGS. 8A, 8B, and 8C illustrate the use of a cuvette of the invention employed in a combination of transmission and reflection to measure optical absorption 800. Any of the geometries shown in FIG. 2 that involve one transmission grating and one reflection grating may be used interchangeably. FIG. 8A illustrates an isometric view, FIG. 8B illustrates a top view, and FIG. 8C illustrates an example of the cuvette employed in FIGS. 8A and 8B. Light enters through a pinhole, is collimated with an off-axis parabolic mirror or other collimating optic (perhaps a lens, in which case the assembly could be linear instead of folded), traverses a beam splitter of conventional design, enters the cuvette through the transmitting grating face, traverses the sample, is reflected from the reflecting grating, re-traverses the sample and transmission grating, is reflected by the beam splitter, and then light is focused by a lens onto an observation plane, preferably equipped with an array detector such as a CMOS camera array or CCD array. Optionally the area observed by the array and lens through the beam splitter via transmission is coated black or is fitted with a beam dump so as to provide a dark backdrop.

FIG. 8A shows a case in which an embodiment based on FIG. 2A and FIG. 2B is employed, with the incident side of the cuvette defined by the direction of incident collimated light 801. Collimated light incident 801 approaches the transmitting side of the cuvette, reflects off the second diffraction grating, returns through the transmitting grating, and returns in the direction from which it came. The effective absorption path length is approximately twice the distance in the transmission cuvette, with path length varying in a predictable way from order to order and wavelength to wavelength. Absorption path length is the distance through the solution parallel to the initial path of the light times the refractive index of the solution divided by the cosine of the angle the diffracted beam makes with the original propagation direction. Upon reflecting from the reflection grating, the light returns, potentially along a different path than that taken originally, depending on the diffraction order and orientation of the second grating. The light then traverses the transmission grating and is diffracted a third time. Three diffraction events inside a spectrometer is less common than single diffraction events, but triple spectrographs have been available for many years. A transmission/reflection/transmission sequence with each surface diffracting has not been previously reported.

The cuvette, with either a reference solution or a solution whose spectrum is to be determined, is inserted into a spectrometer seen in top view (FIG. 8B) or in perspective view (FIG. 8C). Light from a suitable source (fiber optic, arc lamp, light emitting diode, incandescent bulb, laser, or other source) enters through a limiting aperture 702, typically a circular pinhole of diameter between 1 micrometer and 1 millimeter. Light is then collimated with a mirror or lens, here shown as an off-axis parabolic mirror 703. Light next traverses a beam splitter 802 of conventional design, such that approximately half the light proceeds essentially undeviated and the other half is reflected out of the spectrometer, possibly to a beam dump, black-painted surface, or other optical cul de sac. The collimated light that has gone straight through the beam splitter then traverses a cuvette of the invention ((100), oriented so the transmitting face 101 is closest to the mirror and beam splitter). After traversing the cuvette, reflecting off the rear mirror, and retraversing the transmitting grating, the light impinges once again on the beam splitter 802. Half the light is transmitted back towards the focusing mirror, pinhole, and original light source, while the other half is reflected. This light is focused by a mirror or lens, here shown as a lens 704 and is detected with a detector, typically a charge coupled array detector (CCD), CMOS detector, or other electronic camera 705. The appearance of the multiple diffraction orders is approximately cylindrically-symmetrical.

Additional Geometries for Other Types of Spectrometry

The invention has been described in detail for measurement of optical absorption of samples contained in the cuvette. The cuvette with attached gratings may be used as a grating assembly in its own right, with the cuvette filled by vacuum, air, or any transparent liquid. In this instance, light from some optical experiment, for example fluorescence, phosphorescence, Raman scattering, or surface Plasmon resonance, is collimated, passed through the cuvette of the current invention, and the light observed as shown in FIG. 7 or FIG. 8. In essence, the invention is employed as a one-use or few-use, disposable diffraction grating.

Application

A common means of quantitatively determining the amount of a sought-for substance in a specimen or sample is absorption spectrometry. In one example of prior art, light from a light source is collimated and allowed to traverse a solution in a cuvette of conventional design. The light is then collected and focused through an aperture after which it is separated according to wavelength, frequency, or energy and the amount of light at each wavelength, frequency, or energy measured with a suitable detector. The changes in light intensity as modified by the presence of the sought-for substance or that substance after reacting with a color-generating or color-removing chemical, indicates the amount of sought-for substance. The cuvette of the current invention combines the functions of cuvette and energy disperser, allowing spectrometers of particularly simple design to be designed, fabricated, and employed. Light from a suitable source is collimated, directed through a cuvette of the disclosed design, and transmitted light is focused onto a detector, typically a two-dimensional camera such as a charge-coupled array or complementary metal oxide on silicon array but not limited to these detector types. The pattern of light intensity as detected by the point, linear, or areal light detector is used to identify or quantify the sought-for substance. After one determination, the cuvette/grating combination may optionally be reused, recycled, or disposed. Reuse entails removing all traces of the prior contents of the cuvette and avoiding damage to the gratings. If disposed or recycled, subsequent measurements are made using a different cuvette but, typically, the same light source, light collimation, light focusing, and detector.

Additionally, the light-dispersing cuvette can be filled with a transparent substance such as water, ethanol, air, or other clear fluid or clear solid, and used exclusively as an energy dispersion device without holding the analyte. In this application, the sought-for substance generates a signal through reflectance, fluorescence, phosphorescence, surface plasmon resonance, chemiluminescence, bioluminescence, or other optical process. The analyte light effuses through a limiting aperture in place of the light of a light source as is commonly employed in an absorption spectrometer. The light is collimated, dispersed by the multiplicity of gratings of the current invention, and imaged with a lens or mirror onto a linear or areal array as previously described.

A common problem with spectrometers is that their diffraction gratings are sensitive to fingerprints, dust, corrosive gasses, and solute deposits from, e.g., ocean water. At least as common is the use of cuvettes as sample holders for spectrophotometers. Plastic cuvettes are commonly employed for single use spectrophotometric measurements. By combining single use cuvettes and single use gratings, degradation of gratings cannot effect analytical precision or accuracy since gratings are discarded after each use. One or more embodiments of the invention allow large scale, economical formation of plastic cuvettes with one or more embossed gratings. If collimated light impinges on the cuvette, absorbance and dispersion can be simultaneously and economically carried out, reducing the number of additional components required in a spectrometer. For example, a white light emitting diode light source could be collimated through a cuvette, the light dispersed by the embossed grating or gratings, and a digital camera or cell phone camera used to obtain an image of a dispersed spectrum. By comparing light transmitted by a sample and that transmitted by the sample after a reactant chemical has been added, the concentration of one or more analytes may be determined using the Beer Lambert Law as is understood by those skilled in the art of chemical analysis.

Example

A plastic cuvette, BrandTech Scientific Inc. catalog number 759070D, made of polystyrene, capacity 2.5 mL, dimensions 12.5 mm×12.5 mm×45 mm, was modified by placing a Mylar double-dispersion grating on each clear face. On one side, the grating was a 12.5 mm×40 mm Rainbow Symphony Store item number 01503 diffraction grating film cut such that the diffraction direction of one axis of the film was parallel to the vertical (long) axis of the cuvette. On the opposite, outside face, the grating was a 12.5 mm×40 mm Rainbow Symphony Store item number 01503 diffraction grating film cut such that the diffraction direction was rotated 30° clockwise from that of the first face. A 5 mW green diode laser, 532 nm wavelength, was shown through the modified cuvette. The diffraction pattern of multiple orders was approximately cylindrically-symmetrical.

A cuvette is formed for use in a spectrometer using stacked, mutually rotated gratings as described in U.S. Pat. No. 8,885,161. Two gratings are used, both double axis gratings, with one grating rotated 30° with respect to the other. Both gratings are impressed on the outside clear walls of the cuvette. Two silicon masters are fabricated, each with 1 micrometer diameter holes on a square grid with 5 microns between hold centers. A polystyrene cuvette 4.5 cm tall, inside cavity 1.0 cm square, with walls canted 0.5°, tapering towards the open end, is obtained from a commercial vendor. A block in which a water/ethylene glycol mixture can be circulated has, placed upon it, with reference edges assisting alignment, one of the silicon master. The cuvette is aligned so that a 4.5 cm long edge is parallel to the line of 1 micron holes on 5 micron centers and slightly more than 4.5 cm long. The other master is attached to a block in which a water/ethylene glycol mixture can be circulated and placed, etched side toward the cuvette, above the cuvette and rotated so that the 5 micron on center aligned holes are rotated 30° clockwise with respect to the 5 on center holes of the first master. Water/ethylene glycol are circulated through the blocks at a temperature of 85° C. while the blocks are pushed together with a pressure of approximately 200 kilopascals (a mass of 10 kg bearing on a surface area of 5.625 square centimeters=5.625×10-4 square meters). When the cuvette and masters reach about 85° C., force is increased to between 2 and 5 megapascals for a period of approximately 1 second, corresponding to a mass of 27 kilograms to 67 kilograms. Pressure is released, after which the temperature of the stacked components is reduced to 20° C. The stack is disassembled, leaving a cuvette with gratings impressed on both outside faces.

For a dispersive optical spectrometer to be useful, it must be calibrated for wavelength and intensity response. A characteristic of mutually-rotated, double-dispersion gratings is that calibration can be obtained in real time and at point of use, rather than only under carefully controlled conditions. The disclosed invention allows for real time calibration, can optionally be reused or used only once, and thus may have application for biological samples where cross-contamination is to be avoided or with toxic materials where post-use handling is undesirable.

While particular elements, embodiments, and applications of the present invention have been shown and described, the invention is not limited thereto because modifications may be made by those skilled in the art, particularly in light of the foregoing teaching. It is therefore contemplated by the application to cover such modifications and incorporate those features which come within the spirit and scope of the invention.

What is claimed is:
1. An instrument comprising:
a limiting aperture;
a collimating optic;
a container comprising a plurality of walls;
a detector;
wherein a wall of the plurality of walls has a plurality of faces;

wherein among the plurality of faces of a wall of the plurality of walls, a first face of a wall of the plurality of walls comprises a first diffraction grating, a second face of a wall of the plurality of walls comprises a second diffraction grating, and the first face of a wall of the plurality of walls and the second face of a wall of the plurality of walls are not both a common face of a common wall of the plurality of walls;

wherein the collimating optic collimates electromagnetic radiation admitted by the limiting aperture;

wherein the first face and the second face of a wall of the plurality of walls are orientable with respect to the collimating optic and the detector such that the collimated electromagnetic radiation traverses a path which encounters the first face of a wall of the plurality of walls, the second face of a wall of the plurality of walls, and the detector; and wherein the first diffraction grating is a transmission grating and the second diffraction grating is a reflection grating.

2. The instrument of claim 1, wherein the collimated electromagnetic radiation crosses the first face of a wall of the plurality of walls in a first direction, then reflects off the second face of a wall of the plurality of walls, and then crosses the first face in a second direction.

3. The instrument of claim 2, further comprising a receptacle, wherein inserting the container into the receptacle orients the first face of a wall of the plurality of walls and the second face of a wall of the plurality of walls such that the collimated electromagnetic radiation crosses the first face of a wall of the plurality of walls, the second face of a wall of the plurality of walls, and the detector.

4. The instrument of claim 2, wherein the container further comprises a handling member.

5. The instrument of claim 1, wherein at least one wall of the plurality of walls comprises a light-admitting wall.

6. The instrument of claim 1, wherein at least one diffraction grating comprises an additive layer overlaying a face of a wall of the plurality of walls.

7. The instrument of claim 1, wherein at least one diffraction grating comprises a periodic surface relief pattern disposed upon a face of a wall of the plurality of walls.

8. The instrument of claim 1, wherein at least one diffraction grating comprises a periodic line pattern disposed upon a face of a wall of the plurality of walls.

9. The instrument of claim 1, wherein the reflection grating is a partially transmitting reflection grating.

* * * * *